US012733872B2

(12) United States Patent
Kang et al.

(10) Patent No.: US 12,733,872 B2
(45) Date of Patent: Sep. 15, 2026

(54) METHOD OF DISEASE MANAGEMENT USING VOICE DATA AND APPARATUS FOR PERFORMING THE METHOD

(71) Applicant: WELT CORP., LTD, Seoul (KR)

(72) Inventors: Seong Ji Kang, Seoul (KR); Hye Kang Roh, Seoul (KR); Joo Young Kim, Seoul (KR); Do Hyun Lee, Gyeonggi-do (KR); Hwa Young Jeong, Incheon (KR)

(73) Assignee: WELT CORP., LTD, Seoul (KR)

( * ) Notice: Subject to any disclaimer, the term of this patent is extended or adjusted under 35 U.S.C. 154(b) by 350 days.

(21) Appl. No.: 18/522,320

(22) Filed: Nov. 29, 2023

(65) Prior Publication Data

US 2025/0040877 A1 Feb. 6, 2025

(30) Foreign Application Priority Data

Aug. 4, 2023 (KR) ........................ 10-2023-0102207

(51) Int. Cl.
*G10L 15/22* (2006.01)
*A61B 5/00* (2006.01)
*G06F 40/253* (2020.01)
*G06F 40/30* (2020.01)
*G10L 25/66* (2013.01)

(52) U.S. Cl.
CPC ............ *A61B 5/4803* (2013.01); *G10L 15/22* (2013.01); *G10L 25/66* (2013.01)

(58) Field of Classification Search
CPC ..... G06F 40/253; G06F 40/30; A61B 5/4803; G10L 15/22; G10L 25/66
USPC .................................... 704/9, 207, 251, 257
See application file for complete search history.

(56) References Cited

U.S. PATENT DOCUMENTS

| | | | | |
|---|---|---|---|---|
| 11,398,243 B2 * | 7/2022 | Hauptman | ............... | A61B 5/02 |
| 12,159,647 B1 * | 12/2024 | Churgin | .................. | G10L 17/14 |
| 2006/0020447 A1 * | 1/2006 | Cousineau | .............. | G10L 15/26 704/E15.045 |

(Continued)

FOREIGN PATENT DOCUMENTS

| | | |
|---|---|---|
| KR | 10-2016-0142949 A | 12/2016 |
| KR | 10-2298330 B1 | 9/2021 |

(Continued)

OTHER PUBLICATIONS

Voleti R, Liss JM, Berisha V. A Review of Automated Speech and Language Features for Assessment of Cognitive and Thought Disorders. IEEE J Sel Top Signal Process. Feb. 2020; 14(2):282-298. doi: 10.1109/jstsp.2019.2952087. (Year: 2020).*

(Continued)

*Primary Examiner* — Richemond Dorvil
*Assistant Examiner* — Rodrigo A Chavez
(74) *Attorney, Agent, or Firm* — ZION IP; Byungwoong Park

(57) ABSTRACT

A method of disease management using voice data and an apparatus for performing the method can including receiving, by a voice based disease management device, user's voice data. The method and apparatus can also include generating, by the voice based disease management device, disease management data based on the voice data. Optionally, the step of generating disease management data can include extracting context data and out-of-context data based on the voice data.

1 Claim, 7 Drawing Sheets

(56) References Cited

U.S. PATENT DOCUMENTS

| | | | | |
|---|---|---|---|---|
| 2016/0117940 | A1* | 4/2016 | Gomory | G09B 19/04<br>434/262 |
| 2019/0124441 | A1* | 4/2019 | Dong | A61B 5/6897 |
| 2020/0075040 | A1* | 3/2020 | Provost | G10L 25/63 |
| 2020/0219529 | A1* | 7/2020 | Gordon | G10L 15/183 |
| 2020/0294527 | A1* | 9/2020 | Shallom | G10L 15/183 |
| 2021/0113099 | A1* | 4/2021 | Rogers | A61B 5/02055 |
| 2021/0118329 | A1* | 4/2021 | Medan | A61B 5/486 |
| 2021/0118465 | A1* | 4/2021 | Rentoumi | A61B 5/7475 |
| 2021/0153772 | A1* | 5/2021 | Venneti | A61B 5/7203 |
| 2023/0113656 | A1* | 4/2023 | Omiya | G10L 25/21<br>704/270 |
| 2023/0172526 | A1* | 6/2023 | Lipsmeier | A61B 5/4082 |
| 2025/0266036 | A1* | 8/2025 | Kosek | A61B 5/4803 |

FOREIGN PATENT DOCUMENTS

| | | | |
|---|---|---|---|
| KR | 10-2022-0012470 | A | 2/2022 |
| KR | 10-2358902 | B1 | 2/2022 |
| KR | 10-2425479 | B1 | 7/2022 |
| KR | 10-2023-0006110 | A | 1/2023 |
| KR | 10-2023-0020246 | A | 2/2023 |

OTHER PUBLICATIONS

Audre Arlene Anthony, Chandreshekar Mohan Patil, and Jagadeesh Basavaiah. 2022. A Review on Speech Disorders and Processing of Disordered Speech. Wirel. Pers. Commun. 126, 2 (Sep. 2022), 1621-1631. https://doi.org/10.1007/s11277-022-09812-w (Year: 2022).*

Office Action for KR 10-2023-0102207 dated Feb. 6, 2024.

International Search Report for PCT/KR2023/012016 dated Apr. 23, 2024.

* cited by examiner

FIG. 1

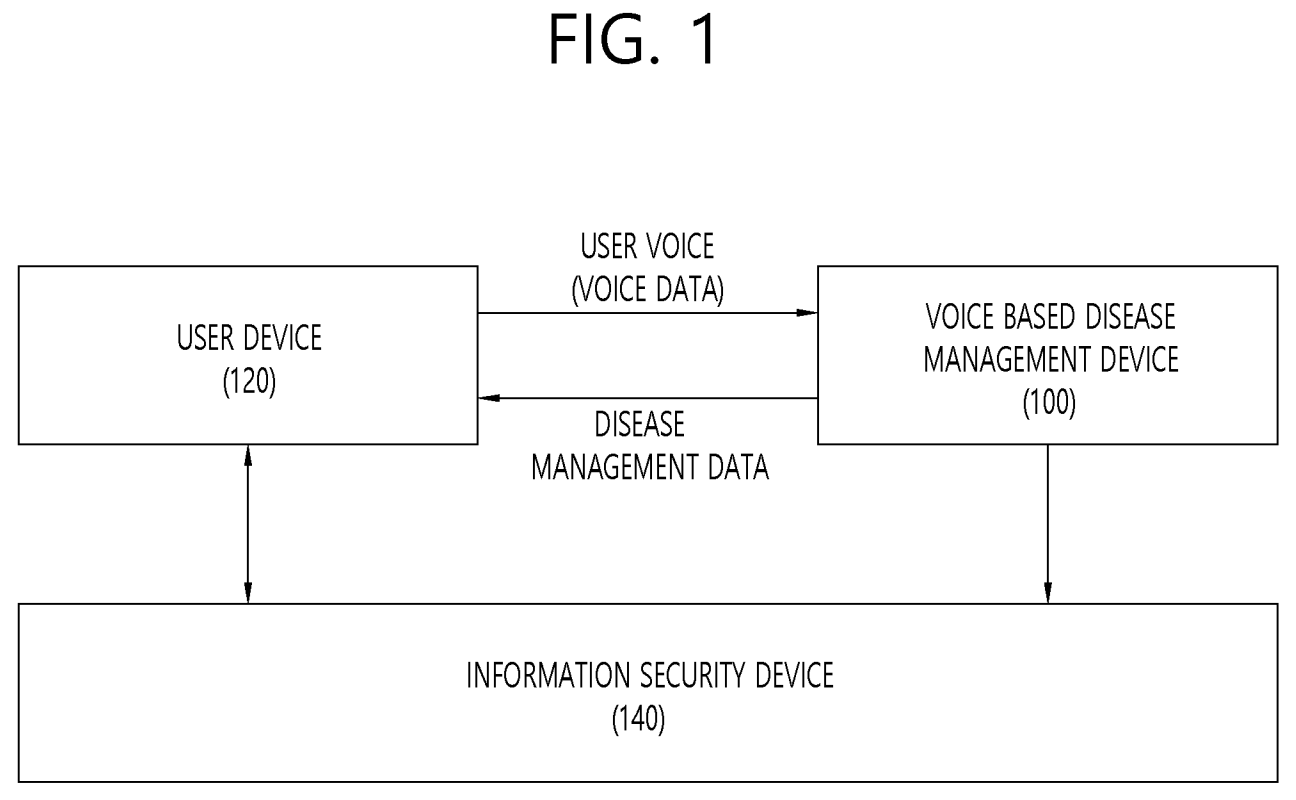

VOICE BASED DISEASE MANAGEMENT DEVICE (100)

USER VOICE (VOICE DATA)

DISEASE MANAGEMENT DATA

USER DEVICE (120)

INFORMATION SECURITY DEVICE (140)

FIG. 6

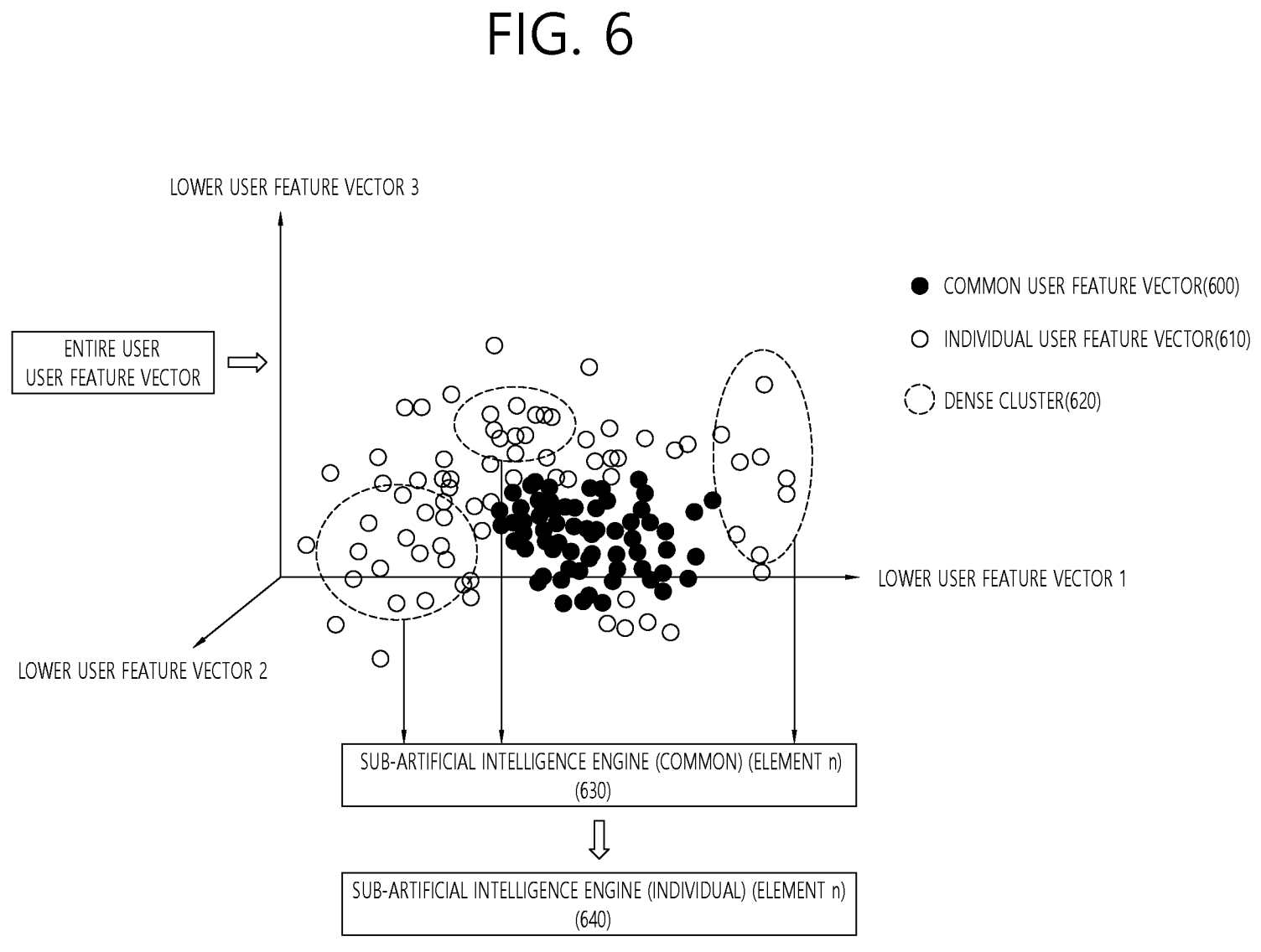

LOWER USER FEATURE VECTOR 3

ENTIRE USER
USER FEATURE VECTOR

COMMON USER FEATURE VECTOR(600)

INDIVIDUAL USER FEATURE VECTOR(610)

DENSE CLUSTER(620)

LOWER USER FEATURE VECTOR 1

LOWER USER FEATURE VECTOR 2

SUB-ARTIFICIAL INTELLIGENCE ENGINE (COMMON) (ELEMENT n)
(630)

SUB-ARTIFICIAL INTELLIGENCE ENGINE (INDIVIDUAL) (ELEMENT n)
(640)

METHOD OF DISEASE MANAGEMENT USING VOICE DATA AND APPARATUS FOR PERFORMING THE METHOD

CROSS-REFERENCE TO RELATED APPLICATION

This application claims priority to and the benefit of Korean Patent Application No. 10-2023-0102207, filed on Aug. 4, 2023, the disclosure of which is incorporated herein by reference in its entirety.

BACKGROUND

1. Field of the Invention

The present invention relates to a method of disease management using voice data and an apparatus for performing the method. More particularly, the present invention relates to a disease management method for a disease that can be analyzed based on voice data and an apparatus for performing the method.

2. Discussion of Related Art

With the development of various smart technologies, data of personal daily activities is recorded, and individual life can be efficiently managed on the basis of the recorded data. In the meantime, health-related data logging is attracting attention due to the increasing interest in healthcare. Many users have already been generating and utilizing various health-related data including data on exercise, diet, sleep, and the like through user devices such as smartphones, wearable devices, and the like. In the past, health-related data was generated and managed only by medical institutions, but now users have begun to generate and manage their own health-related data through user devices such as smartphones and wearable devices.

In many cases, health-related data logging is performed through a wearable device. A wearable device is a user device that is carried by or attached to a user. Due to the development of Internet of things (IoT) and the like, wearable devices are frequently used for collecting health-related data. A wearable device may collect a user's physical change information and surrounding data of the user through equipment and provide advice required for the user's healthcare on the basis of the collected data.

A user's health-related data may include a user biomarker, and research is ongoing on a method of making a medical prescription adaptively to a user on the basis of the user's health-related data.

As related art, there is Korean Patent No. 10-2425479.

SUMMARY OF THE INVENTION

An object of the present invention is to solve all of the above problems.

The present invention is directed to predicting a user's disease based on the user's voice data and performing disease management that monitors the user's disease.

The present invention is also directed to managing a user's disease based on the user's voice data and performing customized disease management for the user by reflecting characteristics of voice data of a specific user and a specific user group.

According to an aspect of the present invention, there is provided a method of disease management using voice data, comprises receiving, by a voice based disease management device, user's voice data; and generating, by the voice based disease management device, disease management data based on the voice data.

Meanwhile, the generating of the disease management data includes extracting, by the voice based disease management device, context data and out-of-context data based on the voice data; and generating, by the voice based disease management device, the disease management data based on the context data and out-of-context data extracted based on the voice data.

Further, the context data is characteristic data generated on a context including sentence completeness, word composition, or a vocabulary, and the out-of-context data is characteristic data generated out of the context including a tone, a pitch, or a stuttering level.

According to another aspect of the present invention, there is provided a voice based disease management device for performing disease management using voice data, wherein the voice based disease management device is implemented to receive user's voice data and generate disease management data based on the voice data.

Meanwhile, the voice based disease management device is implemented to extract context data and out-of-context data based on the voice data; and generate the disease management data based on the context data and out-of-context data extracted based on the voice data.

Further, the context data is characteristic data generated on a context including sentence completeness, word composition, or a vocabulary, and the out-of-context data is characteristic data generated out of the context including a tone, a pitch, or a stuttering level.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 1 is a conceptual diagram illustrating a voice based disease management system according to an embodiment of the present invention.

FIG. 6 is a conceptual diagram illustrating a method of tuning an AI engine (individual) according to an embodiment of the present invention.

DETAILED DESCRIPTION OF EXEMPLARY EMBODIMENTS

Figure 2:
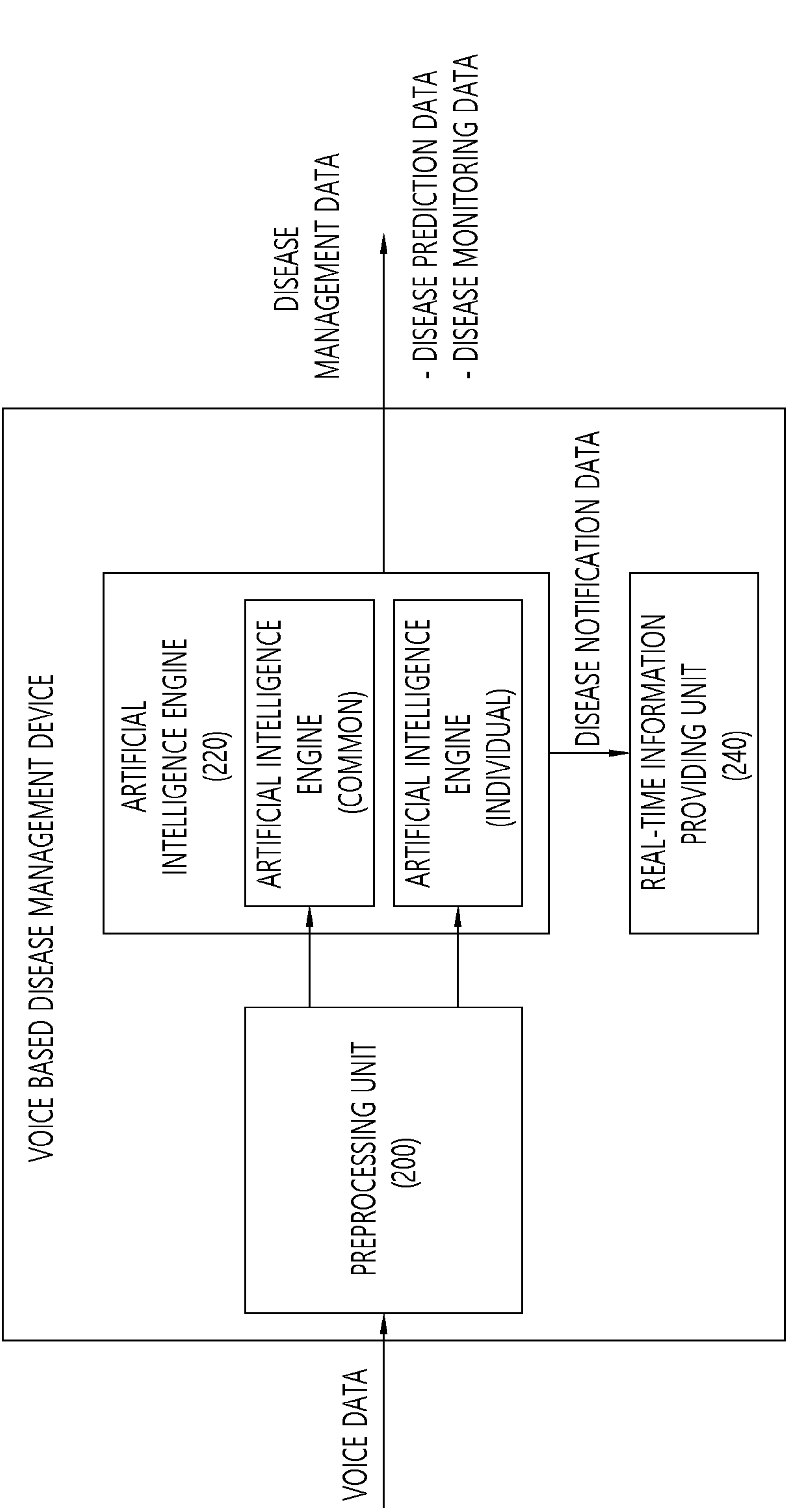
FIG. 2 is a conceptual diagram illustrating a voice based disease management device according to an embodiment of the present invention.

The detailed description of the present invention will be made with reference to the accompanying drawings showing examples of specific embodiments of the present invention. These embodiments will be described in detail such that the present invention can be performed by those skilled in the art. It should be understood that various embodiments of the present invention are different but are not necessarily mutually exclusive. For example, a specific shape, structure, and characteristic of an embodiment described herein may be implemented in another embodiment without departing from the scope and spirit of the present invention. In addition, it should be understood that a position or arrangement of each component in each disclosed embodiment may be changed without departing from the scope and spirit of the present invention. Accordingly, there is no intent to limit the present invention to the detailed description to be described below. The scope of the present invention is defined by the appended claims and encompasses all equivalents that fall within the scope of the appended claims. Like reference numerals refer to the same or like elements throughout the description of the figures.

Hereinafter, in order to enable those skilled in the art to practice the present invention, exemplary embodiments of the present invention will be described in detail with reference to the accompanying drawings. FIG. 1 is a conceptual diagram illustrating a voice based disease management system according to an embodiment of the present invention.

FIG. 1 discloses a voice based disease management system for managing disease based on a user's voice.

Referring to FIG. 1, the voice based disease management system may include a voice based disease management device 100, a user device 120, and an information security device 140.

The voice based disease management device 100 may be a device for managing a user's disease based on an input voice. For example, the voice based disease management device 100 may classify context characteristics and out-of-context characteristics from voice data input by a user, and predict and monitor the user's disease based on the context data and the out-of-context data.

For example, the voice based disease management device 100 may predict and monitor diseases such as migraine and dementia based on the voice.

The user device 120 may transmit a user voice (or voice data) to the voice based disease management device 100 and receive disease management data analyzed based on the user voice. The disease management data may include disease prediction data and disease monitoring data. The disease prediction data may be a predictive value for a disease that a user may have, and the disease monitoring data may be data for monitoring a user's disease.

The information security device 140 may be implemented to secure information generated from the user device 120 and the voice based disease management device 100.

FIG. 2 is a conceptual diagram illustrating a voice based disease management device according to an embodiment of the present invention.

In FIG. 2, a voice based disease management device for generating disease management data by preprocessing voice data is disclosed.

Referring to FIG. 2, the voice based disease management device may include a preprocessing unit 200, an artificial intelligence (AI) engine 220, and a real-time information providing unit 240.

The preprocessing unit 200 may be implemented to preprocess voice data. The voice data may be extracted as context data and out-of-context data through a preprocessing procedure.

The context data may include information on characteristics generated in context, such as sentence completeness, word composition, and a vocabulary.

The out-of-context data may include information on out-of-context characteristics (for example, tone, pitch, a stuttering level, etc.).

An AI engine 220 may receive the context data and the out-of-context data and generate user's disease management data. The disease management data may include disease prediction data and disease monitoring data. For example, the prediction of the possibility of migraine of a user is performed based on the AI engine 220, and information on migraine occurrence time, prescription for reducing migraine, or the like may be provided as disease management data.

The AI engine 220 may include an AI engine (common) and an AI engine (individual). The AI engine (common) may be an engine that does not relatively reflect user characteristics and generate disease management data, and the AI engine (individual) may be an engine that generates disease management data by reflecting relatively more user characteristics. The AI engine (individual) may be an engine generated by separately reflecting user speech characteristics of a specific user or a specific user group. The AI engine (individual) may be an engine that generates the disease management data in consideration of user speech characteristics, such as a usual speaking speed, a tone, and a user's usual word of a specific user or a specific user group.

In addition, the disease management data may include disease alarm data notifying to take action on a disease in real time. For example, when a migraine occurs, disease alarm data for notifying the possibility of migraine and taking action may be transferred to a user device of a user suffering from migraine. Such disease notification data may be provided to a user by the real-time information providing unit 240.

Figure 3:
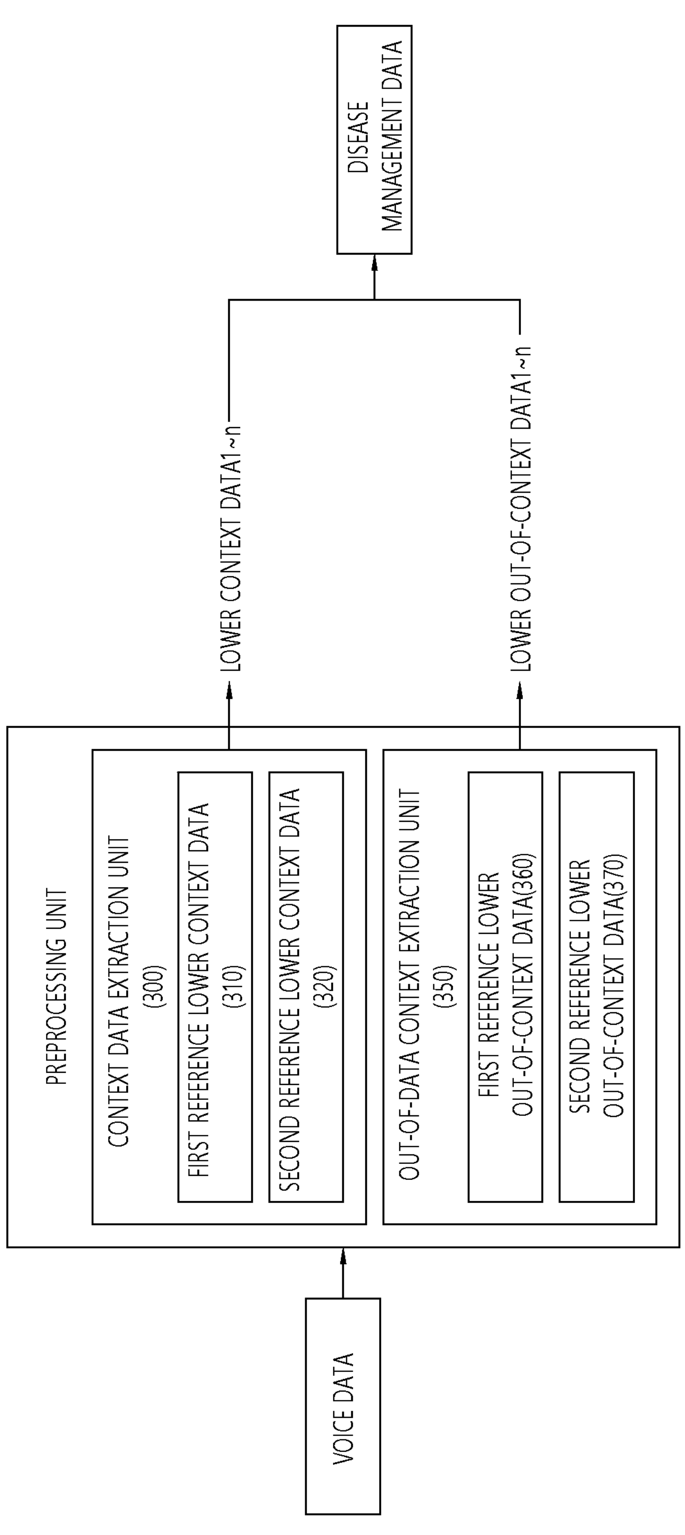
FIG. 3 is a conceptual diagram illustrating a voice based disease management device according to an embodiment of the present invention.

FIG. 3 is a conceptual diagram illustrating a voice based disease management device according to an embodiment of the present invention.

In FIG. 3, a method of preprocessing a voice in a voice based disease management device is disclosed.

Referring to FIG. 3, a preprocessing unit for preprocessing a voice may include a context data extraction unit 300 and an out-of-context data extraction unit 350.

As described above, the context data extraction unit 300 may be implemented to extract data based on contextual meaning of user speech. The out-of-context data extraction unit 350 may be implemented to extract data on voice characteristics (length, pause, pitch, etc.) of user's speech rather than the contextual meaning of the user's speech.

A plurality of lower context data may be extracted from the context data extraction unit 300. The plurality of lower context data may include data for context analysis, such as sentence completion, vocabulary appropriateness, sentence repetition, and word repetition.

In order to extract the out-of-context data by the out-of-context data extraction unit 350, voice sound data may be extracted, and lower out-of-context data 1 to lower out-of-context data n may be extracted from the voice sound data. Each of the lower out-of-context data 1 to the lower out-of-context data n may match out-of-context data such as a tone, a pitch, and a stuttering level.

In the present invention, two pieces of reference lower context data (first reference lower context data 310 and second reference lower context data 320) may exist in order to extract user's lower context data.

The first reference lower context data 310 may be lower context data commonly possessed by users having a critical ratio (e.g., 80%) or more among users having a specific disease. For example, the first reference lower context data 310 may be lower context data commonly appearing in users having dementia or migraine. The first reference lower context data may be adaptively changed according to the accumulation of user's voice data. The first reference lower context data may be set as a separate default value in consideration of a user's age, educational background, sex, and the like.

The second reference lower context data 320 may be lower context data excluding the first reference lower context data. The second reference lower context data 320 may be lower context data observed in a specific user or a specific user group having a specific disease.

The user's voice data may be analyzed based on the first reference lower context data 310 and the second reference lower context data 320, and the disease management data may be generated based on the analysis result.

Similarly, in the present invention, in order to extract the user's lower out-of-context data, two pieces of reference lower out-of-context data (first reference lower out-of-context data 360 and second reference lower out-of-context data 370) may exist.

The first reference lower out-of-context data 360 may be lower out-of-context data commonly possessed by users having a critical ratio (e.g., 80%) or more among users with a specific disease. For example, the first reference lower out-of-context data 360 may be lower out-of-context data commonly appearing in users having dementia or migraine. The first reference lower out-of-context data may be adaptively changed according to the accumulation of user's voice data. The first reference lower out-of-context data may be set as a separate default value in consideration of a user's age, educational background, sex, and the like.

The second reference lower out-of-context data 370 may be lower out-of-context data excluding the first reference lower out-of-context data. The second reference lower out-of-context data 370 may be lower out-of-context data observed in a specific user or a specific user group having a specific disease.

The user's voice data may be analyzed based on the first reference lower out-of-context data 360 and the second reference lower out-of-context data 370, and the disease management data may be generated based on the analysis result.

Figure 4:
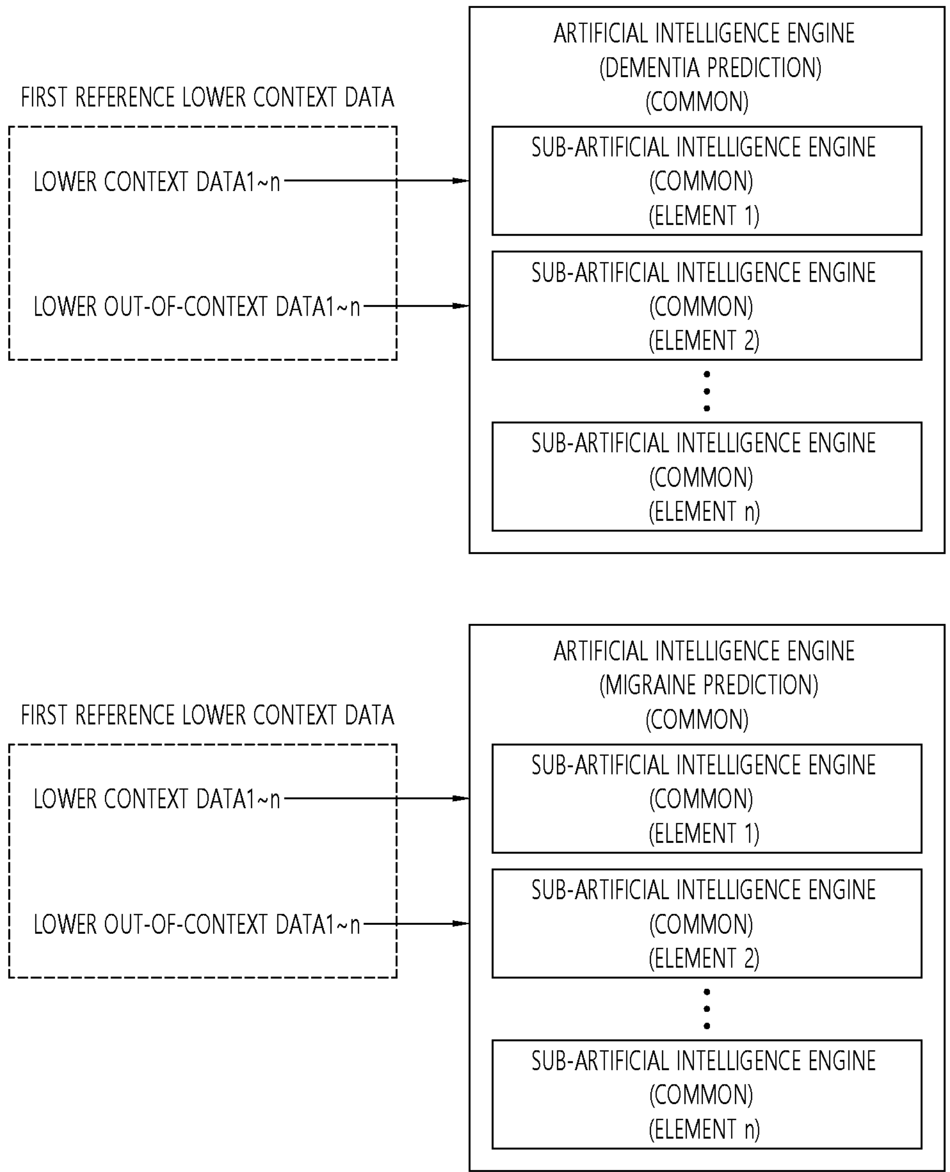
FIG. 4 is a conceptual diagram illustrating a method of generating an AI engine according to an embodiment of the present invention.

FIG. 4 is a conceptual diagram illustrating a method of generating an AI engine according to an embodiment of the present invention.

In FIG. 4, a method of generating an AI engine (common) is disclosed.

Referring to FIG. 4, the AI engine (common) may include at least one sub-AI engine (common) for generating disease management data based on at least one of lower context data or lower out-of-context data.

For example, a sub-AI engine (common) for generating disease management data based on an input for sentence completion data, and a sub-AI engine (common) for generating disease management data based on an input for stuttering data may be individually included in the AI engine (common).

In the present invention, the AI engine (common) may be generated based on a combination of required sub-AI engines (common). For example, the AI engine (common) for migraine prediction may be generated through a combination of sub-AI engines (common) required for migraine prediction of a user. As another example, the AI engine (common) for dementia prediction may be generated through a combination of sub-AI engines (common) required for dementia determination of a user.

An AI engine (common) for predicting a specific disease may be trained based on common training data for predicting a specific disease. For example, the AI engine (common) for migraine prediction may be trained based on lower context data and lower out-of-context data that have generated during migraine, and perform migraine prediction based on lower context data and lower out-of-context data that are input later. As another example, the AI engine (common) for dementia prediction may be trained based on lower context data and lower out-of-context data that have generated during dementia, and perform dementia prediction based on lower context data and lower out-of-context data that are input later.

For convenience of description, an example of an AI engine (common) for predicting a specific disease is presented, but an AI engine (common) for predicting a plurality of diseases may be generated, and this embodiment may also be included within the scope of the present invention.

The training data input to the AI engine (common) may be data for training a disease corresponding to the AI engine (common).

The AI engine (common) is trained and generated based on user's lower context data and user's lower out-of-context data preprocessed based on the first reference lower context data and the first reference lower out-of-context data.

As described above, the first reference lower context data and the first reference out-of-context data may be lower context data and lower out-of-context data commonly possessed by users having a critical ratio (e.g., 80%) or more among users having a specific disease.

The first reference lower context data may vary, and when the first reference lower context data is changed, the AI engine (common) may also be changed. The first reference lower context data may vary, and the change in the first reference lower context data may be determined based on accumulated embedding values on an embedding plane of a user feature vector to be described later. Similarly, the first reference lower out-of-context data may vary, and when the first reference lower out-of-context data is changed, the AI engine (common) may also be changed.

Figure 5:
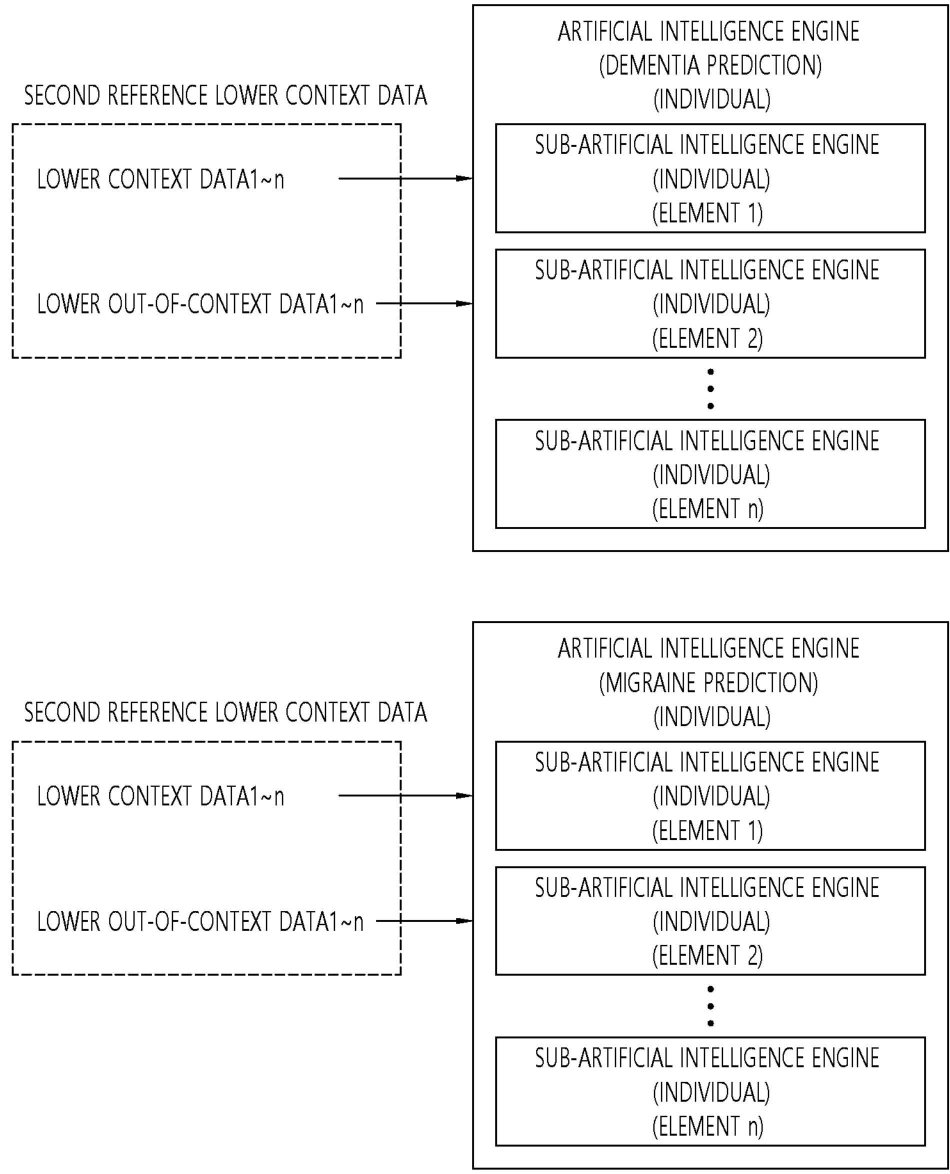
FIG. 5 is a conceptual diagram illustrating a method of generating an AI engine (individual) according to an embodiment of the present invention.

FIG. 5 is a conceptual diagram illustrating a method of generating an AI engine (individual) according to an embodiment of the present invention.

In FIG. 5, an AI engine (individual) tuned (or generated) by separately considering user's speech characteristics is disclosed.

Referring to FIG. 5, the AI engine (individual) may be implemented to determine voice data generated based on a user group including a plurality of users as well as one user by reflecting user characteristics and user group characteristics and generate disease management data.

The AI engine (individual) may include at least one sub-AI engine (individual) for generating disease management data based on at least one of lower context data or lower out-of-context data. The at least one sub-AI engine (individual) may be an engine generated by tuning a sub-AI engine (common) in consideration of characteristics of a user or a user group.

For example, the sub-AI engine (individual) for generating disease management data based on an input for sentence completion data, and the sub-AI engine (individual) for generating disease management data based on an input for stuttering data may be individually included in the AI engine (individual).

In the present invention, the AI engine (individual) may be generated based on a combination of required sub-AI engines (individual). The AI engine (individual) may be generated based on at least one sub-AI engine (common) and sub-AI engine (common). Hereinafter, for convenience of description, it is assumed that the AI engine (individual) is generated based on a combination of required sub-AI engines (individual).

For example, the AI engine (individual) for migraine prediction may be generated through a combination of sub-AI engines (individual) required for migraine prediction of a user. As another example, the AI engine (individual) for dementia prediction may be generated through a combination of sub-AI engines (individual) required for dementia determination of a user.

An AI engine (individual) for predicting a specific disease may be trained based on training data for each user or user group for predicting a specific disease.

The AI engine (individual) may be trained and generated based on user's lower context data and user's lower out-of-context data preprocessed based on the second reference lower context data and the second reference lower out-of-context data.

As described above, the second reference lower context data and the second reference out-of-context data may be lower context data and lower out-of-context data of specific users and specific user groups having a specific disease.

The second reference lower context data may vary, and when the second reference lower context data is changed, the AI engine (individual) may also vary. Similarly, the second reference lower out-of-context data may vary, and when the second reference lower out-of-context data is changed, the AI engine (individual) may also be changed.

FIG. 6 is a conceptual diagram illustrating a method of tuning an AI engine (individual) according to an embodiment of the present invention.

In FIG. 6, a method of generating an AI engine (individual) by tuning an AI engine (common) is disclosed.

Referring to FIG. 6, additional training may be performed on data of a user and a user group for an AI engine (common).

User feature vectors (for example, a vocabulary vector, a sound feature vector, etc.) of all users having a specific disease may be located on the embedding plane. The user feature vector may be a vector extracted based on user's voice data. Among the user feature vectors on the embedding plane, a common user feature vector exclusion procedure for excluding a vector corresponding to the first reference lower context data and a common user feature vector 600 corresponding to the first reference lower out-of-context data may be performed.

Thereafter, the remaining user feature vectors may be defined as an individual user feature vector 610, and a dense cluster 620 may be formed through clustering of the individual user feature vector 610. A user corresponding to the user feature vector included in the dense cluster 620 may be defined as one user group. Depending on the size of the set dense cluster 620 and the density that determines the dense cluster 620, a sub-AI engine (common) (element n) 630 may be further subdivided and divided into a sub-AI engine (individual) (element n) 640. If necessary, the size of the dense cluster 620 is adjusted to be relatively small for a specific element (or a user vector (e.g., a vocabulary vector) of a specific dimension) and the density determining the dense cluster 620 is adjusted to be relatively small, so the sub-AI engine (individual) (element n) 640 may be determined through relatively more division.

For example, a first user group corresponding to a first dense cluster may be defined. Based on the user feature vector for the first user group, additional training may be performed on the sub-AI engine (common) (element n) 630, and the sub-AI engine (common) (element n) may vary to the sub-AI engine (individual) (element n) 640.

In addition, in the present invention, the user feature vector commonly possessed by users of critical criteria on the embedding plane is changed according to the accumulation of user feature vectors of user data (or user's voice data) having a specific disease, and thus, the first reference lower out-of-context data corresponding to the first reference lower out-of-context data may vary. As described above, when the vector corresponding to the first reference lower context data according to the accumulation of user feature vectors of all users having a specific disease and the first reference lower out-of-context data is changed, the AI engine (common) and the sub-AI (common) may vary. The AI engine (individual) and the sub-AI engine (individual) may also vary according to the change in the AI engine (common) and the sub-AI engine (common).

Figure 7:
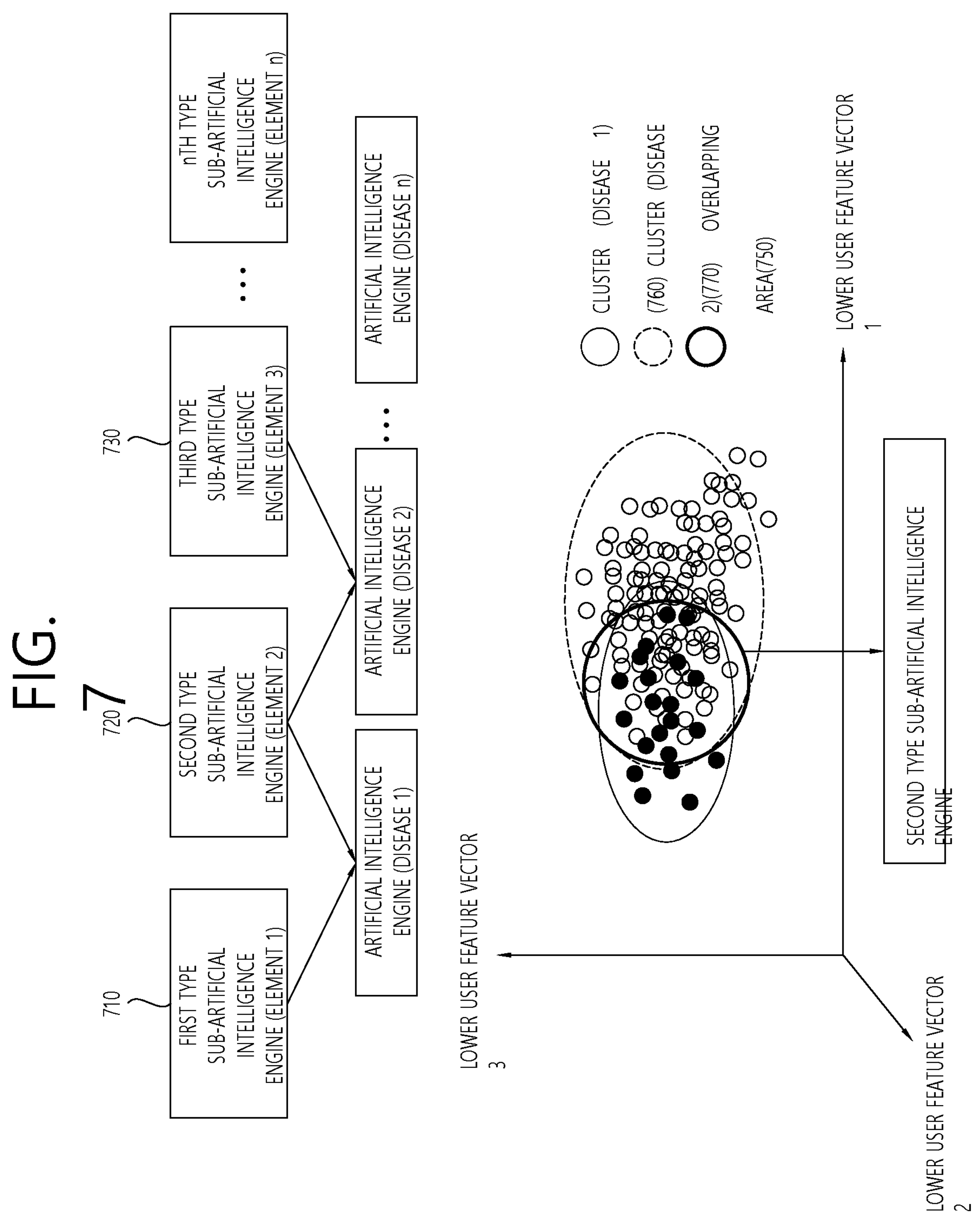
FIG. 7 is a conceptual diagram illustrating a relationship between a sub-AI engine and an AI engine according to an embodiment of the present invention.

FIG. 7 is a conceptual diagram illustrating a relationship between a sub-AI engine and an AI engine according to an embodiment of the present invention.

FIG. 7 discloses a method of applying a plurality of different sub-AI intelligence engines to a specific disease (or different disease).

Referring to FIG. 7, the same sub-AI engine may be applied and utilized to an AI engine for diagnosing different diseases. For example, the sub-AI engine (stuttering determination) may be used as a sub-AI engine for dementia prediction or a sub-AI engine for migraine prediction.

A sub-AI engine used only for a specific disease may be expressed as a first type sub-AI engine 710, and a sub-AI engine that may be used for various diseases may be expressed as a second type sub-AI engine 720. The first type sub-AI engine 710 may be trained based on voice data of a user having a specific disease. The second type sub-AI engine 720 may be trained based on voice data of a user having different diseases.

For the training of the second type sub-AI engine 720, user feature vectors located in an overlapping area 750 among user feature vectors embedded based on voice data of a user having different diseases may be used. Among the user feature vectors, the overlapping area 750 may be determined based on a cluster (disease 1) 760 for disease 1 and a cluster (disease 2) 770 for disease 2 by individually clustering user feature vectors of users having different diseases. An area where cluster (disease 1) 760 and cluster (disease 2) 770 overlap may be determined to be the overlapping area 750, and training based on user feature vectors located in the overlapping area 750 may be performed.

The embodiments of the present invention described above may be implemented in the form of program instructions that can be executed through various computer units and recorded on computer readable media. The computer readable media may include program instructions, data files, data structures, or combinations thereof. The program instructions recorded on the computer readable media may be specially designed and prepared for the embodiments of the present invention or may be available instructions well known to those skilled in the field of computer software. Examples of the computer readable media include magnetic media such as a hard disk, a floppy disk, and a magnetic tape, optical media such as a compact disc read only memory (CD-ROM) and a digital video disc (DVD), magneto-optical media such as a floptical disk, and a hardware device, such as a ROM, a RAM, or a flash memory, that is specially made to store and execute the program instructions. Examples of the program instruction include machine code generated by a compiler and high-level language code that can be executed in a computer using an interpreter and the like. The hardware device may be configured as at least one software module in order to perform operations of embodiments of the present invention and vice versa.

While the present invention has been described with reference to specific details such as detailed components, specific embodiments and drawings, these are only examples to facilitate overall understanding of the present invention and the present invention is not limited thereto. It will be understood by those skilled in the art that various modifications and alterations may be made.

Therefore, the spirit and scope of the present invention are defined not by the detailed description of the present invention but by the appended claims, and encompass all modifications and equivalents that fall within the scope of the appended claims.

What is claimed is:

1. A computer-implemented method of training at least two AI (artificial intelligence) engines for performing disease management using voice data, wherein the at least two AI engines comprise a common AI engine and an individual AI engine, the method comprising:

collecting user's voice data;

preprocessing the user's voice data;

extracting context data and out-of-context data from the voice data, wherein the context data is characteristic data generated on a context including sentence completeness, word composition, or a vocabulary, and the out-of-context data is characteristic data generated out of the context including a tone, a pitch, or a stuttering level;

extracting a plurality of first lower context data from the context data based on a first reference lower context data;

extracting a plurality of first lower out-of-context data from the out-of-context data based on a first reference lower out-of-context data;

training the common AI engine using the plurality of first lower context data and the plurality of first lower out-of-context data;

extracting a plurality of second lower context data from the context data based on a second reference lower context data;

extracting a plurality of second lower out-of-context data from the out-of-context data based on a second reference lower out-of-context data; and training the individual AI engine using the plurality of second lower context data and the plurality of second lower out-of-context data, wherein the first reference lower context data is a data appears, with a predetermined ratio including percentage of eighty or more, in users having a specific disease, the second reference lower context data is a data observed in a specific user or a specific user group having the specific disease, excluding the first reference lower context data, the first reference lower out-of-context data is a data appears, with the predetermined ratio including percentage of eighty or more, in the users having the specific disease, the second reference lower out-of-context data is a data observed in the specific user or the specific user group having the specific disease, excluding the first reference lower out-of-context data, and the first reference lower context data and the first reference lower out-of-context data are adaptively changed according to an accumulation of the user's voice data.

* * * * *